(12) United States Patent
Matsumura et al.

(10) Patent No.: US 7,312,357 B2
(45) Date of Patent: Dec. 25, 2007

(54) PROCESS FOR PRODUCING ALIPHATIC DICARBOXYLIC ACID COMPOUND

(75) Inventors: Yoshihiro Matsumura, Nagasaki (JP); Osamu Onomura, Nagasaki (JP); Fumiaki Iwasaki, Yamaguchi (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 10/599,171

(22) PCT Filed: Mar. 23, 2005

(86) PCT No.: PCT/JP2005/005986

§ 371 (c)(1),
(2), (4) Date: Sep. 21, 2006

(87) PCT Pub. No.: WO2005/092821

PCT Pub. Date: Oct. 6, 2005

(65) Prior Publication Data

US 2007/0276156 A1    Nov. 29, 2007

(30) Foreign Application Priority Data

Mar. 26, 2004    (JP)    ............................. 2004-090983

(51) Int. Cl.
*C07C 51/245*    (2006.01)
*C07C 51/27*    (2006.01)

(52) U.S. Cl. ..................................... 562/528; 562/540
(58) Field of Classification Search ..................... None
See application file for complete search history.

(56) References Cited

FOREIGN PATENT DOCUMENTS

| JP | 2001 213841 A | 8/2001 |
| JP | 2002 226421 A | 8/2002 |

OTHER PUBLICATIONS

Organic Synthesis; pp. 18-20, 1941.
Thurnal Organischeskoi Khimii; pp. 488-494 and a partial English translation, 1988.

*Primary Examiner*—Paul A. Zucker
(74) *Attorney, Agent, or Firm*—Norris McLaughlin & Marcus PA

(57) ABSTRACT

The present invention discloses a process for producing an aliphatic dicarboxylic acid compound, which comprises oxidizing, with a nitrite or a nitrate in the presence of trifluoroacetic acid, an alicyclic secondary alcohol compound or an alicyclic ketone compound, in each of which at least one methylene group is bonded to the carbon atom having hydroxyl group bonded thereto or the carbon atom as a member of carbonyl group, wherein the reaction is conducted in the presence of water of 5 mass % or less relative to 100 mass % of the total of the trifluoroacetic acid and the water.

6 Claims, No Drawings

PROCESS FOR PRODUCING ALIPHATIC DICARBOXYLIC ACID COMPOUND

TECHNICAL FIELD

The present invention relates to a process for producing an aliphatic dicarboxylic acid compound, which comprises oxidizing an alicyclic secondary alcohol compound or an alicyclic ketone compound with a nitrite or a nitrate in the presence of trifluoroacetic acid.

BACKGROUND ART

Carboxylic acid compounds are important industrially as raw materials for drugs, agricultural chemicals or dyes. Of the carboxylic acid compounds, dicarboxylic acid compounds are extremely important as a raw material monomer for production of high-molecular compounds.

Meanwhile, oxidation reaction using nitric acid or a nitrate is an oxidation reaction which is extremely important in organic synthesis. This oxidation reaction using nitric acid or a nitrate is ordinarily used as a process for oxidizing an alicyclic secondary alcohol compound into an aliphatic dicarboxylic acid derivative. In particular, a process of oxidizing cyclohexanol with nitric acid in the presence of ammonium vanadate is known as the most popular oxidation process using nitric acid (Organic Synthesis, Vol. 1, pp. 18-20, 1932).

However, in the above oxidation process using nitric acid, there is a fear that the oxidation reaction proceeds rapidly. Therefore, addition of cyclohexanol to nitric acid containing ammonium vanadate need be conducted very cautiously and the temperature control need be made strictly. Further, since a carbon-to-carbon bond cleavage reaction proceeds in the course of the oxidation reaction, the yield of the adipic acid obtained remains at about 58 to 60%. Thus, this production process is not fully satisfactory.

On the other hand, as a process for oxidizing an alcohol compound into an aldehyde compound or a ketone compound, there is a process which comprises oxidizing an alcohol compound into an aldehyde compound or a ketone compound in an aqueous solution containing 90 volume % (93.1 mass %) of trifluoroacetic acid, using sodium nitrite or sodium nitrate as an oxidizing agent (Thurnal Organischeskoi Khimii, Vol. 24, pp. 488-495, 1988).

This oxidation reaction which is conducted in an aqueous solution containing 90 volume % of trifluoroacetic acid, using a nitrite or a nitrate, is a very mild oxidation reaction which proceeds at room temperature. By this process, an alicyclic secondary alcohol compound can be oxidized into an alicyclic ketone compound almost quantitatively. With this process, however, it is impossible to further oxidize the alicyclic ketone compound obtained, into an aliphatic dicarboxylic acid.

DISCLOSURE OF THE INVENTION

In view of the above fact, the present inventors made a study on a process for producing an aliphatic dicarboxylic acid under mild conditions. As a result, it was found that, in the oxidation reaction conducted using a nitrite or a nitrate in the presence of trifluoroacetic acid, the amount of water present in the reaction system had a large influence on the progress of the oxidation reaction. As a result of a further study, the present invention has been completed.

Hence, the present invention aims at providing a process for producing an aliphatic dicarboxylic acid compound at a high selectivity, at a high yield and in a safe operation.

The present invention is described below.

[1] A process for producing an aliphatic dicarboxylic acid compound, which comprises oxidizing, with a nitrite or a nitrate in the presence of trifluoroacetic acid, an alicyclic secondary alcohol compound or an alicyclic ketone compound, in each of which at least one methylene group is bonded to the carbon atom having hydroxyl group bonded thereto or the carbon atom as a member of carbonyl group, wherein the reaction is conducted in the presence of water of 5 mass % or less relative to 100 mass % of the total of the trifluoroacetic acid and the water.

[2] A process for producing an aliphatic dicarboxylic acid compound according to [1], wherein the alicyclic secondary alcohol compound or the alicyclic ketone compound is a 3- to 12-membered cyclic compound.

[3] A process for producing an aliphatic dicarboxylic acid compound according to [1], wherein the amount of the nitrite or nitrate used is 0.5 to 10 moles relative to 1 mole of the alicyclic secondary alcohol compound or the alicyclic ketone compound.

[4] A process for producing an aliphatic dicarboxylic acid compound according to [1], wherein the concentration of the alicyclic secondary alcohol compound or the alicyclic ketone compound in trifluoroacetic acid is 0.05 to 60 mass %.

[5] A process for producing an aliphatic dicarboxylic acid compound according to [1], wherein the alicyclic secondary alcohol compound is cyclohexanol.

[6] A process for producing an aliphatic dicarboxylic acid compound according to [1], wherein the alicyclic ketone compound is cyclohexanone.

According to the present invention, an aliphatic dicarboxylic acid compound can be produced from an alicyclic secondary alcohol compound or an alicyclic ketone compound at a high yield under very mild conditions. Therefore, the present invention is extremely useful industrially.

BEST MODE FOR CARRYING OUT THE INVENTION

In the production process of the present invention, an alicyclic secondary alcohol compound or an alicyclic ketone compound is oxidized with a nitrite or a nitrate in the presence of trifluoroacetic acid to produce an aliphatic dicarboxylic acid compound.

(Alicyclic Secondary Alcohol Compound, Alicyclic Ketone Compound)

In the production process of the present invention, there is used, as a starting raw material, an alicyclic secondary alcohol compound represented by the following formula (1), or an alicyclic ketone compound represented by the following formula (2).

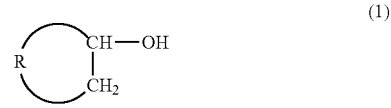

(1)

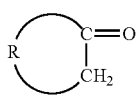

(2)

The alicyclic secondary alcohol compound (1) is an alicyclic alcohol compound wherein at least one methylene group is bonded to the carbon atom having hydroxyl group bonded thereto. The alicyclic ketone compound (2) is an alicyclic ketone compound wherein at least one methylene group is bonded to the carbon atom as a member of carbonyl group. Incidentally, two methylene groups may be bonded to the both sides of the carbon atom having hydroxyl group bonded thereto or of the carbon atom as a member of carbonyl group.

In each of the formulas (1) and (2), R is a bivalent aliphatic group. R is a bivalent aliphatic group having preferably 1 to 10, more preferably 2 to 4 carbon atoms. The aliphatic group R may be a straight chain or a branched chain. The aliphatic group R is preferably a straight chain, particularly preferably a straight chain of 4 carbon atoms. When the aliphatic group R has 4 carbon atoms, the dicarboxylic acid compound obtained is adipic acid which is industrially important as a raw material for nylon.

Or, the aliphatic group R is preferred to have a branch(es) at a position(s) at which the ring thereof shows a symmetric structure. When the aliphatic group R has a branch(s) at a position(s) at which the ring thereof shows a symmetric structure, the dicarboxylic acid compound obtained by the present reaction is a single compound of high purity.

As to the alicyclic secondary alcohol compound (1) or the alicyclic ketone compound (2), there can be selected a compound having a chemical structure corresponding to the chemical structure of the aliphatic dicarboxylic acid compound to be produced. As the compound (1) or (2), a compound available as a reagent or as an industrial raw material can be used with no restriction.

As the alicyclic secondary alcohol compound usable in the present invention, there can be mentioned 3- to 12-membered cyclic compounds such as cyclopropanol, cyclobutanol, cyclopentanol, cyclohexanol, cycloheptanol, cyclooctanol, cyclononanol, cyclodecanol, cycloundecanol, cyclododecanol, 2-methylcyclohexanol, 3-methylcyclohexanol, 2,5-dimethylcyclohexanol, 3,5-dimethylcyclohexnaol, 3,3,5-trimethylcyclohexanol, 2-methylcyclopentanol, 4-methylcyclohexanol, 4-tert-butylcyclohexanol and the like.

As the alicyclic ketone compound, there can be mentioned 3- to 12-membered cyclic compounds such as cyclopropanone, cyclobutanone, cyclopentanone, cyclohexanone, cycloheptanone, cyclooctanone, cyclononanone, cyclodecanone, cycloundecanone, cyclododecanone, 2-methylcyclohexanone, 3-methylcyclohexanone, 2,6-dimethylcyclohexanone, 3,3,5-trimethylcyclohexnaone, 2-ethylcyclhexanone, 4-ethylcyclohexanone, 2-methylcyclopentanone, 4-methylcyclohexanone, 4-tert-butylcyclohexanone and the like.

Of these alicyclic secondary alcohol compounds and alicyclic ketone compounds, preferably used in the present production process are those showing a symmetric molecular structure, that is, alicyclic secondary alcohol compounds such as cyclopropanol, cyclobutanol, cyclopentanol, cyclohexanol, cycloheptanol, cyclooctanol, cyclononanol, cyclodecanol, cycloundecanol, cyclododecanol, 4-methylcyclohexanol, 4-tert-butylcyclohexanol and the like, and alicyclic ketone compounds such as cyclopropanone, cyclobutanone, cyclopentanone, cyclohexanone, cycloheptanone, cyclooctanone, cyclononanone, cyclodecanone, cycloundecanone, cyclododecanone, 4-methylcyclohexanone, 4-ethylcyclohexanone, 4-tert-butylcyclohexanone and the like. By using each of these compounds as a raw material compound, the reaction product obtained is a single compound.

(Nitrite, Nitrate)

As the nitrite and nitrate used in the present invention, there can be used compounds available industrially or as a reagent, with no restriction.

As specific examples of these compounds, there can be mentioned, as the nitrite, sodium nitrite, potassium nitrite, lithium nitrite and silver nitrite.

As the nitrate, there can be mentioned, for example, ammonium nitrate, ammonium cerium nitrate, lithium nitrate, potassium nitrate, sodium nitrate, cesium nitrate, nickel nitrate, samarium nitrate, strontium nitrate, silver nitrate, zinc nitrate, copper nitrate and lead nitrate.

Of these nitrites and nitrates, particularly preferred are nitrites such as sodium nitrite, potassium nitrite, lithium nitrite, silver nitrite and the like. Since these compounds form nitrogen monoxide cation having a high oxidation power in the reaction system, there can be produced an intended aliphatic dicarboxylic acid compound at a high yield.

The amount of the nitrite or nitrate used differs depending upon the atmosphere of the reaction and therefore can not be set at a given level. However, with a small amount, the oxidation reaction hardly proceeds and, with an excessive amount, the post-operation is complicated. Therefore, the preferred amount of the nitrite or nitrate used is ordinarily 0.5 to 10 mols, particularly 0.7 to 7 mols relative to 1 mol of the alicyclic secondary alcohol compound or alicyclic ketone compound used as a reaction raw material.

(Trifluoroacetic Acid)

The trifluoroacetic acid used in the present invention functions as a reaction catalyst and also as a solvent.

There is no particular restriction as to the amount of trifluoroacetic acid used. However, a small amount results in a reduction in the yield of oxidation reaction and a large amount requires a complicated post-operation. Therefore, it is preferred that trifluoroacetic acid is used so that the concentration of alicyclic secondary alcohol compound or alicyclic ketone compound becomes ordinarily 0.05 to 60 mass %, preferably 0.1 to 30 mass %.

The biggest feature of the present invention lies in that, in oxidizing an alicyclic secondary alcohol compound or an alicyclic ketone compound with a nitrite or a nitrate in the presence of trifluoroacetic acid, the amount of water present in the reaction system is kept at 5 mass % or less relative to the total amount (100 mass %) of trifluoroacetic acid and water.

When the water amount in the reaction system is more than the above level, the oxidation reaction proceeds to a ketone compound and stops at this point, making it impossible to obtain an aliphatic dicarboxylic acid compound at a good yield. In order to achieve a certain efficiency in the oxidation reaction, the presence of a larger amount of water tends to require a larger amount of a nitrite or a nitrate. Meanwhile, time and labor are needed in order to make the reaction system water-free. Therefore, in the production process of the present invention, the amount of water is preferably 0.001 to 3 mass %, more preferably 0.01 to 1 mass % in view of the efficiency of oxidation reaction and the time and labor for removal of water from reaction system.

In the production process of the present invention, reduction of water is easy for the cyclic secondary alcohol compound or the cyclic ketone compound as a raw material or for the nitrite or nitrate as an oxidizing agent, and the water contents in these compounds are extremely low when these are used as reagents or commercial products available as industrial raw materials. Therefore, the effect of the water, which is derived from the compounds, on the water amount of reaction system is slight. Actually, the trifluoroacetic acid, when a reagent or a commercial product available as an industrial raw material is used therefor, contains less than 3 mass % of water ordinarily and less than 1 mass % at most.

Thus, in the production process of the present invention, it is most practical to use reagents or industrial raw materials available through an ordinary route, per se. Of course, dehydration may be conducted as necessary by a known method.

(Reaction Conditions)

There is no particular restriction as to the reaction temperature. However, with a high reaction temperature, the oxidation reaction becomes violent and the reaction system tends to reach a dangerous state. With a low reaction temperature, the reaction time becomes strikingly long. Therefore, the reaction temperature is preferably the melting point of trifluoroacetic acid to 60° C., particularly preferably 0 to 40° C.

The reaction time differs depending upon the kind of the alicyclic secondary alcohol compound or alicyclic ketone compound used, and also differs depending upon the kind and amount of the nitrite or nitrate used. However, the reaction time is ordinarily 0.1 to 30 hours.

The reaction can be carried out under any of normal pressure, reduced pressure or applied pressure. The reaction can be carried out not only in the presence of oxygen (e.g. oxygen or air) but also in the presence of inert gas (e.g. nitrogen, argon or carbon dioxide). However, the reaction in the presence of oxygen tends to save the use amount of nitrite or nitrate and further shorten the reaction time. Ordinarily, the reaction is carried out in the air or an oxygen atmosphere.

In the production process of the present invention, the alicyclic secondary alcohol compound or alicyclic ketone compound as a raw material is oxidized into an aliphatic dicarboxylic acid compound according to the following reaction formula.

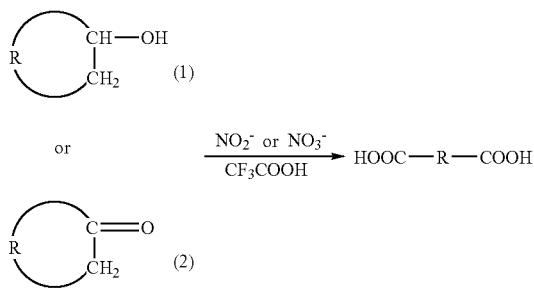

As described above, in the above reaction formula, R is a bivalent aliphatic group. The R is preferably a bivalent aliphatic group having 1 to 10 carbon atoms, which is a straight chain or has a branch at a position where the ring thereof shows a symmetric structure.

As to the method for isolating and purifying an aliphatic dicarboxylic acid compound from the thus-obtained reaction product, there is no particular restriction, and a known method can be used.

For example, after the completion of the reaction, trifluoroacetic acid (which is a reaction solvent) is distilled off under reduced pressure, at room temperature. Then, to the residue obtained is added an aqueous solution containing 5% of sodium hydrogencarbonate to obtain an aqueous basic solution. Thereafter, extraction is conducted using methylene chloride to remove the organic solvent-soluble components. To the aqueous solution obtained is added 10% hydrochloric acid to make the aqueous solution acidic. Then, water is distilled off under reduced pressure. Thereafter, an aqueous ethyl acetate solution is added to the residue obtained, to dissolve the residue. Insoluble components are removed by filtration and the filtrate is subjected to distillation under reduced pressure, whereby can be obtained an intended aliphatic dicarboxylic acid compound.

The obtained aliphatic dicarboxylic acid compound is a single compound when there is used, as a raw material, an alicyclic secondary alcohol compound or an alicyclic ketone compound, both having a symmetric molecular structure. In contrast, in the conventional known nitric acid oxidation process, a plurality of different aliphatic dicarboxylic acids compound are formed. In the production process of the present invention, there is no substantial formation of a plurality of different aliphatic dicarboxylic acids and this is the biggest feature of the present production process.

Incidentally, the production process of the present invention can be applied not only to the oxidation reaction for production of an aliphatic dicarboxylic acid compound from an alicyclic secondary alcohol compound or an alicyclic ketone compound, but also to the oxidation reaction for production of a carboxylic acid compound from a primary alcohol compound or an aldehyde compound.

EXAMPLES

The present invention is described specifically below by way of Examples. However, the present invention is in no way restricted by such Examples.

Example 1

In a 50-ml eggplant type flask was placed, as an alicyclic secondary alcohol compound, 100 mg (1 mmol) of cyclohexanol (special grade chemical produced by Wako Pure Chemical Industries, ltd., water content: 100 ppm or less). Thereto was added, as a solvent, 5 ml of trifluoroacetic acid (special grade chemical produced by Wako Pure Chemical Industries, Ltd., purity: 98% or more, water content: 0.1 mass %) to dissolve cyclohexanol.

Dry air was bubbled into the trifluoroacetic acid solution in which cyclohexanol had been dissolved, for 15 minutes with ice-cooling. Then, there was added, as a nitrite, 138 mg (2 mmol) of sodium nitrite (special grade chemical produced by Wako Pure Chemical Industries, ltd.). Stirring was conducted for 30 minutes in this state and then for 4 hours and 30 minutes at room temperature to give rise to a reaction. After the completion of the reaction, the majority of trifluoroacetic acid was distilled off at room temperature under reduced pressure (30 mmHg). Then, to the resulting residue was added an aqueous solution containing 5 mass % of sodium hydrogencarbonate, to dissolve the residue, whereby was obtained an aqueous basic solution. This aqueous basic solution was subjected to extraction with methylene chloride (15 ml×3) to extract unreacted materials. The methylene chloride was dried over magnesium sulfate and distilled off for examination of the presence of cyclohexanone. However, no cyclohexanone was detected.

To the remaining aqueous solution was added 10% hydrochloric acid to make the solution acidic. Then, water was distilled off under reduced pressure. To the resulting residue was added 30 ml of ethyl acetate for dissolution. Magnesium sulfate was added to the resulting ethyl acetate solution for drying. The magnesium sulfate was removed by filtration and the filtrate was subjected to distillation under reduced pressure to remove ethyl acetate, whereby was obtained 146 mg (yield: 100%) of 1,4-butanedicarboxylic acid.

Examples 2 to 7

An operation was conducted in the same manner as in Example 1 except that sodium nitrite was replaced by a nitrite or nitrate shown in Table 1. The results are shown in Table 1.

TABLE 1

| Example No. | Nitrite or nitrate (equivalents) | Yield of 1,4-ethanedicarboxylic acid (%) | Yield of cyclohexanone (%) |
|---|---|---|---|
| 2 | Sodium nitrite (5) | 100 | 0 |
| 3 | Sodium nitrite (1) | 69 | 25 |
| 4 | Potassium nitrite (2) | 100 | 0 |
| 5 | Sodium nitrate (2) | 84 | 0 |
| 6 | Sodium nitrate (5) | 100 | 0 |
| 7 | Potassium nitrate (5) | 100 | 0 |

Examples 8 to 23

An operation was conducted in the same manner as in Example 2 except that cyclohexanol was replaced by an alicyclic secondary alcohol compound or an alicyclic ketone compound, both shown in Table 2 as a raw material compound. The results are shown in Table 2.

TABLE 2

| Example No. | Raw material compound | Reaction time (hr) | Product (yield %) |
|---|---|---|---|
| 8 | Cyclobutanol | 5 | 1,2-Ethanedicarboxylic acid (100) |
| 9 | Cyclopentanol | 12 | 1,3-Propanedicarboxylic acid (85) Cyclopentanone (10) |
| 10 | Cycloheptanol | 12 | 1,5-Pentanedicarboxylic acid (80) Cycloheptanone (18) |
| 11 | Cyclooctanol | 5 | 1,6-hexanedicarboxylic acid (94) |
| 12 | Cyclodecanol | 5 | 1,8-octanedicarboxylic acid (98) |
| 13 | Cyclododecanol | 10 | 1,10-Decanedicarboxylic acid (90) |
| 14 | 4-Methylcyclohexanol | 5 | 2-Methyl-1,4-butanedicarboxylic acid (100) |
| 15 | 3-Methylcyclohexanol | 5 | 2-Methyl-1,4-butanedicarboxylic acid (60) 1-Methyl-1,4-butanedicarboxylic acid (30) |
| 16 | 4-Tert-butylcyclohexanol | 5 | 2-Tert-butyl-1,4-butanedicarboxylic acid (92) |
| 17 | Cyclobutanone | 5 | 1,2-Ethanedicarboxylic acid (100) |
| 18 | Cyclopentanone | 5 | 1,3-Propanedicarboxylic acid (95) |
| 19 | Cyclohexanone | 5 | 1,4-Butanedicarboxylic acid (100) |
| 20 | Cycloheptanone | 5 | 1,5-Pentanedicarboxylic acid (98) |
| 21 | 4-Tert-butylcyclohexanone | 5 | 2-Tert-butyl-1,4-butanedicarbxylic acid (98) |
| 22 | Cyclooctanone | 5 | 1,6-Hexanedicarboxylic acid (98) |
| 23 | 4-Methylcyclohexanone | 5 | 2-Methyl-1,4-butanedicarboxylic acid (100) |

Example 24

In a 50-ml eggplant type flask was placed 100 mg (1 mmol) of cyclohexanol (special grade chemical produced by wako Pure Chemical Industries, Ltd.) as an alicyclic secondary alcohol compound. Thereto was added, as a solvent, 5 ml of trifluoroacetic acid (special grade chemical produced by Wako Pure Chemical Industries, ltd., purity: 98% or more) to dissolve cyclohexanol. Oxygen was bubbled into trifluoroacetic acid for 15 minutes with ice-cooling. Then, there was added, as a nitrite, 69 mg (1 mmol) of sodium nitrite (special grade chemical produced by Wako Pure Chemical Industries, ltd.). An oxygen balloon was fitted to the flask, and stirring was conducted for 30 minutes and then at room temperature for 4 hours and 30 minutes.

After the completion of the reaction, the majority of trifluoroacetic acid was distilled off at room temperature under reduced pressure (30 mmHg). Then, to the resulting residue was added an aqueous solution of 5 mass % of sodium hydrogencarbonate. To this aqueous basic solution was added methylene chloride (15 ml×3) to extract unreacted materials. The collected methylene chloride was dried over magnesium sulfate; methylene chloride was distilled off; and the presence of cyclohexanone therein was examined. As a result, no cyclohexanone was detected. To the remaining aqueous solution was added 10% hydrochloric acid to make the solution acidic. Then, water was distilled off under reduced pressure. To the resulting residue was added 30 ml of ethyl acetate for dissolution. Magnesium sulfate was added to the resulting ethyl acetate solution for drying. The magnesium sulfate was removed by filtration and the filtrate was subjected to distillation under reduced pressure to remove ethyl acetate, whereby was obtained 145 mg (yield: 99%) of 1,4-butanedicarboxylic acid.

Comparative Example 1

An operation was conducted in the same manner as in Example 1 except that trifluoroacetic acid containing 0.1 mass % of water was replaced by an aqueous solution containing 93.1 mass % (90 volume %) of trifluoroacetic acid and that cyclohexanone was used as a raw material for reaction. As a result, no adipic acid (intended product) was obtained and cyclohexanone used as a raw material was recovered quantitatively.

The invention claimed is:

1. A process for producing an aliphatic dicarboxylic acid compound, which comprises oxidizing, with a nitrite or a nitrate in the presence of trifluoroacetic acid, an alicyclic secondary alcohol compound or an alicyclic ketone compound, in each of which at least one methylene group is bonded to the carbon atom having hydroxyl group bonded thereto or the carbon atom as a member of carbonyl group, wherein the reaction is conducted in the presence of water of 5 mass % or less relative to 100 mass % of the total of the trifluoroacetic acid and the water.

2. A process for producing an aliphatic dicarboxylic acid compound according to claim 1, wherein the alicyclic secondary alcohol compound or the alicyclic ketone compound is a 3- to 12-membered cyclic compound.

3. A process for producing an aliphatic dicarboxylic acid compound according to claim 1, wherein the amount of the nitrite or nitrate used is 0.5 to 10 mols relative to 1 mol of the alicyclic secondary alcohol compound or the alicyclic ketone compound.

4. A process for producing an aliphatic dicarboxylic acid compound according to claim 1, wherein the concentration of the alicyclic secondary alcohol compound or the alicyclic ketone compound in trifluoroacetic acid is 0.05 to 60 mass %.

5. A process for producing an aliphatic dicarboxylic acid compound according to claim 1, wherein the alicyclic secondary alcohol compound is cyclohexanol.

6. A process for producing an aliphatic dicarboxylic acid compound according to claim 1, wherein the alicyclic ketone compound is cyclohexanone.

* * * * *